(12) United States Patent
Mishra et al.

(10) Patent No.: US 8,923,541 B2
(45) Date of Patent: Dec. 30, 2014

(54) TWO-PIECE SOUND PROCESSOR SYSTEM FOR USE IN AN AUDITORY PROSTHESIS SYSTEM

(75) Inventors: Lakshmi N. Mishra, Valencia, CA (US); Joey Chen, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 13/497,906

(22) PCT Filed: Jun. 29, 2011

(86) PCT No.: PCT/US2011/042286
§ 371 (c)(1),
(2), (4) Date: Mar. 23, 2012

(87) PCT Pub. No.: WO2012/099620
PCT Pub. Date: Jul. 26, 2012

(65) Prior Publication Data
US 2014/0146985 A1    May 29, 2014

(51) Int. Cl.
*H04R 25/00* (2006.01)
*A61N 1/36* (2006.01)
*A61N 1/372* (2006.01)

(52) U.S. Cl.
CPC .......... *H04R 25/556* (2013.01); *A61N 1/36032* (2013.01); *A61N 1/37241* (2013.01); *A61N 1/37247* (2013.01)
USPC .......................................... 381/323; 381/314

(58) Field of Classification Search
CPC ........... A61N 1/36032; A61N 1/37211; A61N 1/37217; A61N 1/37235; A61N 1/37247; A61N 1/37252; A61N 1/3787; H04R 25/407; H04R 25/556
USPC ....................... 381/23.1, 312–331; 607/55–57
See application file for complete search history.

(56) References Cited

U.S. PATENT DOCUMENTS

| 5,824,022 A | 10/1998 | Zilberman et al. |
| 6,620,094 B2 | 9/2003 | Miller |

(Continued)

FOREIGN PATENT DOCUMENTS

| AU | 2009/101370 | 3/2013 |
| AU | 2009/101371 | 3/2013 |

(Continued)

OTHER PUBLICATIONS

Final Office Action received in U.S. Appl. No. 13/428,325 dated Nov. 25, 2013.

(Continued)

*Primary Examiner* — Matthew Eason
(74) *Attorney, Agent, or Firm* — ALG Intellectual Property, LLC (57) ABSTRACT

An exemplary system includes 1) a headpiece module configured to be affixed to a head of a patient and comprising a primary sound processor configured to generate stimulation parameters used to direct an auditory prosthesis implanted within the patient to apply electrical stimulation representative of one or more audio signals to the patient and 2) a sound processor module separate from the headpiece module and configured to be selectively and communicatively coupled to the headpiece module. The sound processor module includes a secondary sound processor configured to detect a communicative coupling of the sound processor module to the headpiece module and contribute to the generation of one or more of the stimulation parameters while the sound processor module is communicatively coupled to the headpiece module. Corresponding systems and methods are also disclosed.

18 Claims, 7 Drawing Sheets

(56) References Cited

U.S. PATENT DOCUMENTS

| | | |
|---|---|---|
| 7,174,214 B2 * | 2/2007 | Seligman .................. 607/57 |
| 7,529,587 B2 | 5/2009 | Single |
| 7,599,508 B1 | 10/2009 | Lynch et al. |
| 7,869,883 B2 | 1/2011 | Seligman |
| 8,107,661 B1 | 1/2012 | Lynch et al. |
| 8,170,253 B1 | 5/2012 | Lynch et al. |
| 8,270,647 B2 | 9/2012 | Crawford et al. |
| 8,515,112 B2 | 8/2013 | Crawford et al. |
| 2003/0171787 A1 | 9/2003 | Money et al. |
| 2005/0078846 A1 | 4/2005 | Single |
| 2005/0209657 A1 | 9/2005 | Chung et al. |
| 2007/0282394 A1 | 12/2007 | Segel et al. |
| 2008/0288022 A1 | 11/2008 | Van der Borght et al. |
| 2009/0306742 A1 | 12/2009 | Van Dijk et al. |
| 2011/0098786 A1 | 4/2011 | Mishra et al. |
| 2011/0129106 A1 | 6/2011 | Hasler et al. |
| 2012/0041515 A1 | 2/2012 | Meskens et al. |
| 2012/0226331 A1 | 9/2012 | Banna et al. |
| 2013/0085549 A1 | 4/2013 | Case et al. |

FOREIGN PATENT DOCUMENTS

| | | |
|---|---|---|
| WO | WO-02/056637 | 7/2002 |
| WO | WO-2012/117290 | 9/2012 |

OTHER PUBLICATIONS

Communication pursuant to Article 94(3) EPC received in European Patent Application No. 09835749.4, dated Jun. 4, 2013.

International Search Report and Written Opinion received in International Application No. PCT/US2011/042286 dated Oct. 12, 2011.

Kwan AN, et al., "Design for a Simplified Cochlear Implant System", *IEEE Transactions on Biomedical Engineering*, vol. 54, No. 6, (Jun. 1, 2007).

Non-Final Office Action received in U.S. Appl. No. 13/428,325, dated May 14, 2013.

* cited by examiner

United States Patent US 8,923,541 B2

TWO-PIECE SOUND PROCESSOR SYSTEM FOR USE IN AN AUDITORY PROSTHESIS SYSTEM

BACKGROUND INFORMATION

In the field of auditory prosthesis systems (e.g., cochlear implant systems), there are often two competing requirements—size and performance. For example, auditory prosthesis users would like the smallest devices possible while simultaneously being able to connect to auxiliary audio input devices (e.g., FM transmitters, Bluetooth devices, audio players, etc.), manually adjust various control parameters (e.g., volume, sensitivity, etc.), and/or otherwise enjoy a variety of other features that many auditory prosthesis systems have to offer. Unfortunately, many of these features require specialized hardware (e.g., external interface components, user input mechanisms, etc.) and consume a relatively large amount of power. As a result, the hardware that the user has to wear (e.g., behind or on his or ear) is relatively large, bulky, and aesthetically unpleasing.

SUMMARY

An exemplary system includes 1) a headpiece module configured to be affixed to a head of a patient and comprising a primary sound processor configured to generate stimulation parameters used to direct an auditory prosthesis implanted within the patient to apply electrical stimulation representative of one or more audio signals to the patient and 2) a sound processor module separate from the headpiece module and configured to be selectively and communicatively coupled to the headpiece module. The sound processor module includes a secondary sound processor configured to detect a communicative coupling of the sound processor module to the headpiece module and contribute to the generation of one or more of the stimulation parameters while the sound processor module is communicatively coupled to the headpiece module.

An exemplary headpiece module is configured to be affixed to a head of a patient and includes 1) a primary sound processor configured to generate stimulation parameters used to direct an auditory prosthesis implanted within the patient to apply electrical stimulation representative of one or more audio signals to the patient and 2) communication circuitry communicatively coupled to the primary sound processor configured to transmit the stimulation parameters to the auditory prosthesis. The primary sound processor is further configured to detect a communicative coupling of a sound processor module comprising a secondary sound processor to the headpiece module and allow the secondary sound processor to contribute to the generation of one or more stimulation parameters included in the stimulation parameters while the sound processor module is communicatively coupled to the headpiece module.

An exemplary method includes a primary sound processor included in a headpiece module 1) generating stimulation parameters used to direct an auditory prosthesis implanted within the patient to apply electrical stimulation representative of one or more audio signals to the patient, 2) detecting a communicative coupling of a sound processor module to the headpiece module, the sound processor module separate from the headpiece module and comprising a secondary sound processor, and 3) allowing the secondary sound processor to contribute to the generation of one or more stimulation parameters included in the stimulation parameters while the sound processor module is communicatively coupled to the headpiece module.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

A two-piece sound processor system for use in an auditory prosthesis system is described herein. As will be described in more detail below, the two-piece sound processor system may include a primary sound processor located within a headpiece module configured to be affixed to a head of a patient (or user) and a secondary sound processor located within a sound processor module configured to be worn or carried by the user behind the ear, on the ear, or at any other suitable location. The sound processor module may be configured to be selectively and communicatively coupled to the headpiece module by way of a wired and/or wireless communication link.

In some examples, the primary sound processor may independently generate stimulation parameters used to direct an auditory prosthesis implanted within the patient to apply electrical stimulation representative of one or more audio signals to the patient. However, during periods in which the sound processor module is communicatively coupled to the headpiece module, the secondary sound processor may contribute to the generation of one or more of the stimulation parameters. For example, the secondary sound processor may apply one or more pre-processing functions to an audio signal and then transmit data representative of the pre-processed audio signal to the primary sound processor for further processing, provide connectivity to one or more external devices (e.g., auxiliary audio input devices, fitting devices, etc.), facilitate user adjustment of one or more of the stimulation parameters (e.g., by providing one or more user input mechanisms with which the user may interact), and/or otherwise provide one or more sound processing features not available with the primary sound processor alone. In this manner, the patient may wear the headpiece module only (and thereby enjoy the benefits of not having to wear a sound processor unit on or behind his or her ear) and still be able to enjoy basic auditory prosthesis functionality. When the patient wishes to access additional sound processing features not available with the primary sound processor alone, the patient may simply connect the sound processor module to the headpiece module (e.g., by putting the sound processor module on).

Figure 1:
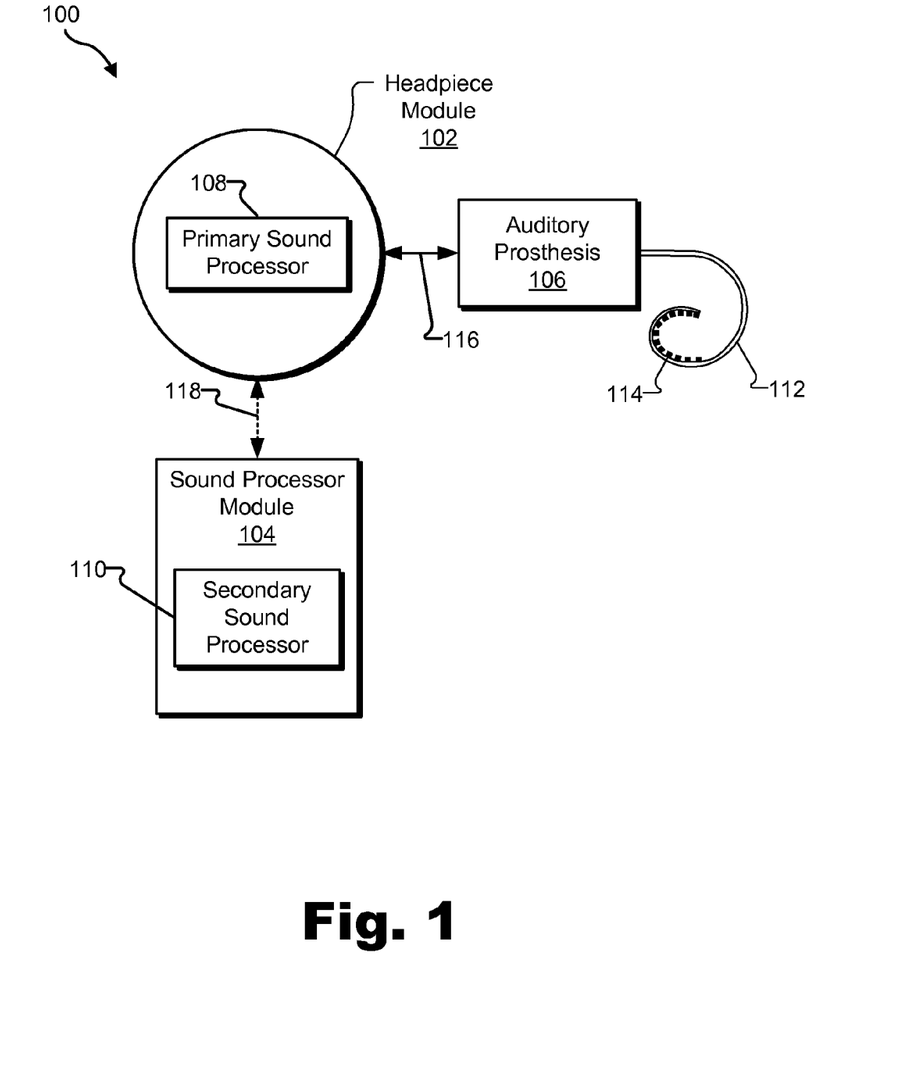
FIG. 1 illustrates an exemplary auditory prosthesis system according to principles described herein.

FIG. 1 illustrates an exemplary auditory prosthesis system 100 (or simply "system 100"). As shown, system 100 may include a headpiece module 102, a sound processor module 104, and an auditory prosthesis 106. Headpiece module 102 may include a primary sound processor 108 disposed therein and sound processor module 104 may include a secondary sound processor 110 therein. Auditory prosthesis 106 may be communicatively coupled to a lead 112 having a plurality of electrodes 114 disposed thereon. Each of the components shown in FIG. 1 will now be described in more detail.

Headpiece module 102 may be configured to be affixed to a patient's head and positioned such that communication circuitry (e.g., a coil) housed within headpiece module 102 is communicatively coupled to corresponding communication circuitry (e.g., a coil) included within auditory prosthesis 106. In this manner, headpiece module 102 may be communicatively coupled to auditory prosthesis 106 in a wireless manner, as illustrated by communication link 116. Headpiece module 102 may be of any suitable shape, size, and form factor as may serve a particular implementation. Various components and features of headpiece module 102 will be described below.

Sound processor module 104 may include any suitable device configured to be worn behind the ear of a patient (i.e., a behind-the-ear device) or off the ear (i.e., a body worn device) of the patient. An exemplary off-the-ear sound processor module 104 may be secured to a piece of clothing worn by the patient, carried in a pocket or pouch, and/or otherwise carried by the patient. Various components and features of sound processor module 104 will be described below.

In some examples, sound processor module 104 may be selectively and communicatively coupled to headpiece module 102 by way of a communication link 118, which may be wired (e.g., implemented by one or more wires, cables, etc.) or wireless as may serve a particular implementation. To illustrate, sound processor module 104 may be selectively and communicatively coupled to headpiece module 102 by plugging sound processor 104 in to headpiece module 102, placing sound processor module 104 within range of headpiece module 102 (e.g., by placing sound processor module 104 behind or on the ear of a patient), turning "on" sound processor module 104, etc.

Auditory prosthesis 106 may be partially or fully implanted within a patient and configured to apply electrical stimulation representative of one or more audio signals by way of one or more of electrodes 114 to one or more stimulation sites associated with an auditory pathway (e.g., the auditory nerve) of the patient. In some examples, auditory prosthesis 106 may apply the electrical stimulation in accordance with stimulation parameters provided thereto by primary sound processor 108. Auditory prosthesis 106 may include any type of implantable stimulator (e.g., cochlear implant, brainstem implant, etc.) that may be used in association with the systems and methods described herein.

Primary sound processor 108 located within headpiece module 102 and secondary sound processor 110 located within sound processor module 104 may together be referred to herein as a "two-piece sound processor system" and may each include or be implemented by any combination of hardware, software, and/or firmware as may serve a particular implementation. For example, primary sound processor 108 and/or secondary sound processor 110 may each include or be implemented by a computing device or processor configured to perform one or more of the functions described herein. Exemplary components and features of primary sound processor 108 and secondary sound processor 110 will now be described.

Figure 2:
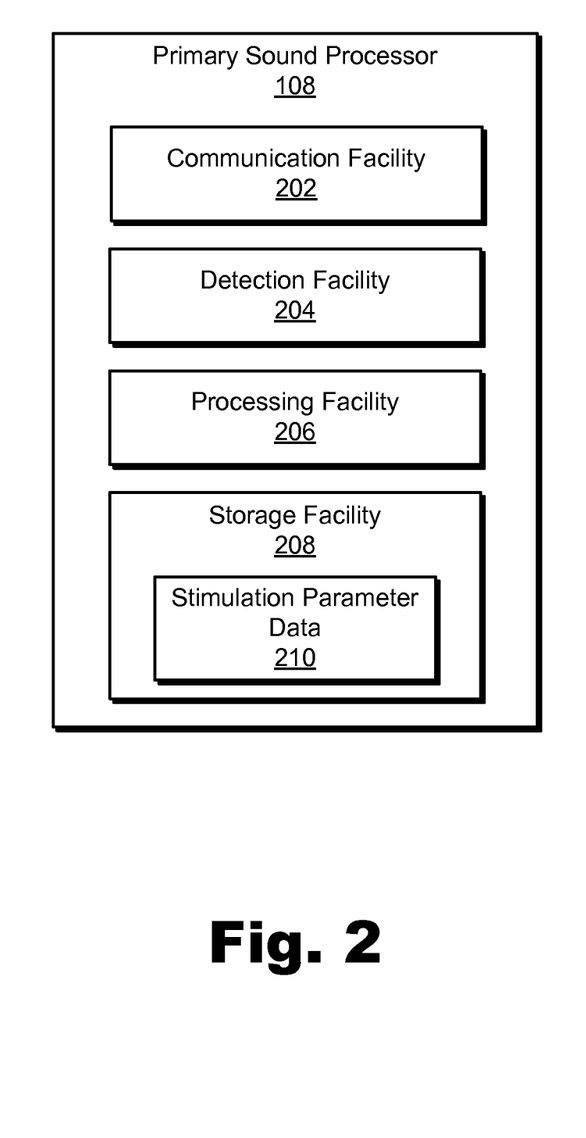
FIG. 2 illustrates exemplary components of a primary sound processor according to principles described herein.

FIG. 2 illustrates exemplary components of primary sound processor 108. As shown in FIG. 2, primary sound processor 108 may include a communication facility 202, a detection facility 204, a processing facility 206, and a storage facility 208, which may be in communication with one another using any suitable communication technologies. These facilities will now be described in more detail.

Communication facility 202 may be configured to facilitate communication between primary sound processor 108 and secondary sound processor 110 and between primary sound processor 108 and auditory prosthesis 106. For example, communication facility 202 may include one or more components configured to receive data from secondary sound processor 110 and/or transmit stimulation parameters to auditory prosthesis 106.

Detection facility 204 may be configured to detect a communicative coupling of sound processor module 104 to headpiece module 102. For example, detection facility 204 may detect that sound processor module 104 has been plugged in to headpiece module 102, placed within range of headpiece module 102, turned on, etc. As will be described below, primary sound processor 108 may be configured to allow secondary sound processor 110 to contribute to the generation of one or more stimulation parameters while sound processor module 104 is communicatively coupled to headpiece module 102.

Detection facility 204 may be further configured to detect a communicative decoupling of sound processor module 104 from headpiece module 102. For example, detection facility 204 may detect that sound processor module 104 has been unplugged from headpiece module 102, removed from being placed within range of headpiece module 102, turned off, etc. As will be described below, primary sound processor 108 may be configured to generate stimulation parameters independent of secondary sound processor 110 while sound processor module 110 is not communicatively coupled to headpiece module 102.

Processing facility 206 may be configured to perform one or more sound processing operations on one or more audio signals presented to an auditory prosthesis patient. For example, processing facility 206 may generate stimulation parameters used to direct auditory prosthesis 106 to apply electrical stimulation representative of one or more audio signals to the patient. One or more of the stimulation parameters may be generated by processing facility 206 independent of secondary sound processor 110. Additionally or alternatively, one or more of the stimulation parameters may be generated by processing facility 206 in conjunction with secondary sound processor 110. For example, processing facility 206 may generate, adjust, and/or otherwise modify one or more stimulation parameters based on data transmitted to primary sound processor 108 by secondary sound processor 110.

Processing facility 206 may be configured to perform any other signal processing operation as may serve a particular implementation. For example, processing facility 206 may detect one or more audio signals presented to a patient, adjust one or more stimulation parameters, and/or transmit one or more stimulation parameters to auditory prosthesis 106.

Storage facility 208 may be configured to maintain stimulation parameter data 210 representative of one or more stimulation parameters that may be transmitted to auditory prosthesis 106. Storage facility 208 may be configured to maintain additional or alternative data as may serve a particular implementation.

Figure 3:
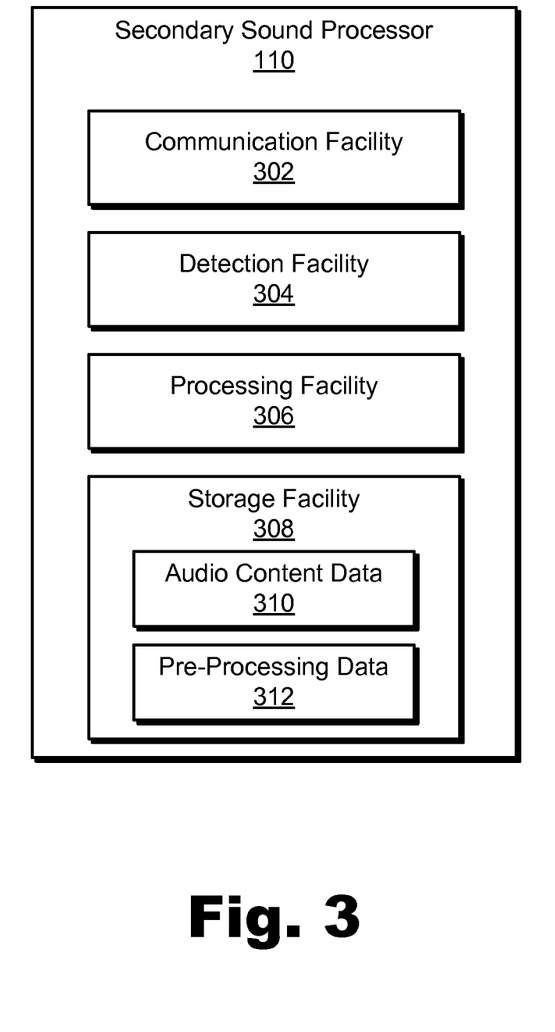
FIG. 3 illustrates exemplary components of a secondary sound processor according to principles described herein.

FIG. 3 illustrates exemplary components of secondary sound processor 110. As shown in FIG. 3, secondary sound processor 110 may include a communication facility 302, a detection facility 304, a processing facility 306, an interface facility 308, and a storage facility 310, which may be in communication with one another using any suitable communication technologies. These facilities will now be described in more detail.

Communication facility 302 may be configured to facilitate communication between secondary sound processor 110 and primary sound processor 108. For example, communication facility 302 may include one or more components configured to transmit data to and/or receive data from primary sound processor 108. Exemplary data that may be transmitted by communication facility 302 to primary sound processor 108 includes data representative of a pre-processed audio signal, fitting data, auxiliary audio input data, etc.

Detection facility 304 may be configured to detect a communicative coupling of sound processor module 104 to headpiece module 102. For example, detection facility 304 may detect that sound processor module 104 has been plugged in to headpiece module 102, placed within range of headpiece module 102, turned on, etc. As mentioned, secondary sound processor 110 may be configured to contribute to the generation of one or more stimulation parameters while sound processor module 104 is communicatively coupled to headpiece module 102.

Processing facility 306 may be configured to contribute to the generation of one or more stimulation parameters by primary sound processor 108 while sound processor module 104 is communicatively coupled to headpiece module 102. For example, as will be illustrated below, sound processor module 104 may include one or more user input mechanisms (e.g., a program selection mechanism, a volume control mechanism, and/or a sensitivity control mechanism) with which a user (e.g., the patient) may interact. Processing facility 306 may detect interaction by a user with one or more user input mechanisms and, in response, adjust one or more stimulation parameters (e.g., by transmitting data to primary sound processor 108 directing primary sound processor 108 to adjust the one or more stimulation parameters).

Additionally or alternatively, processing facility 306 may be configured to contribute to the generation of one or more stimulation parameters by detecting an audio signal presented to a patient, applying one or more pre-processing functions to the audio signal, and transmitting data representative of the pre-processed audio signal to primary sound processor 108. Processing facility 306 may apply a pre-processing function to an audio signal by amplifying the audio signal, converting the audio signal to a digital signal, filtering data representative of the audio signal with a pre-emphasis filter, subjecting data representative of the audio signal to automatic gain control, performing a beam forming function associated with the detection of the audio signal, and/or in any other manner as may serve a particular implementation.

Additionally or alternatively, processing facility 306 may be configured to contribute to the generation of one or more stimulation parameters by processing and/or transmitting data representative of an audio signal provided by an auxiliary audio input device to primary sound processor 108 for further processing. As mentioned, an auxiliary audio input device may include a FM transmitter, a Bluetooth device, an audio player (e.g., an MP3 player), and/or any other type of device configured to provide auxiliary audio input.

Storage facility 308 may be configured to maintain audio content data 310 representative of audio content detected or otherwise received by secondary sound processor 110, pre-processing data 312 representative pre-processing data to be transmitted from secondary sound processor 110 to primary sound processor 108, and/or any other type of data as may serve a particular implementation. Storage facility 308 may be configured to maintain additional or alternative data as may serve a particular implementation.

Figure 4:
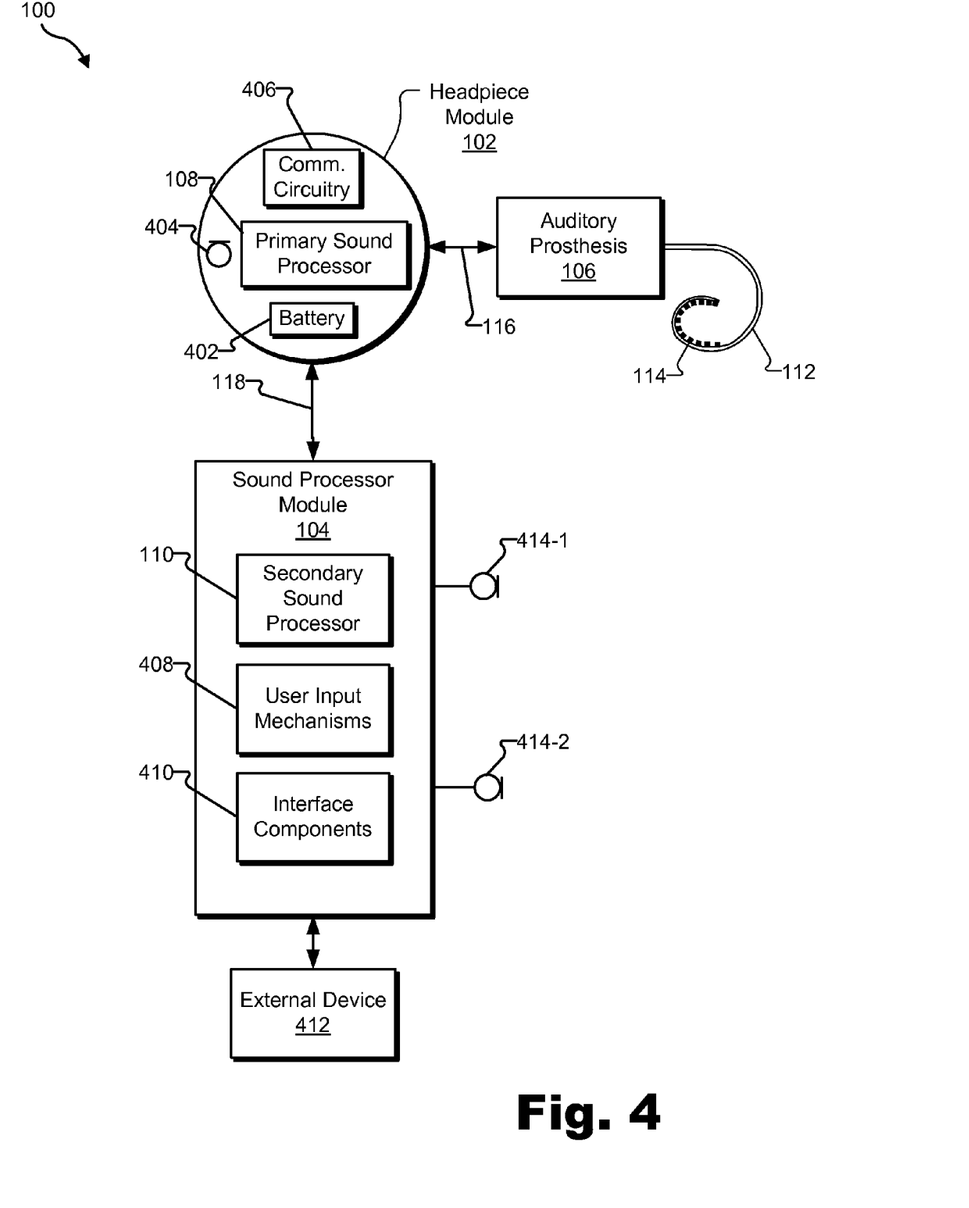
FIGS. 4-6 illustrate various implementations of the auditory prosthesis system of FIG. 1 according to principles described herein.

FIG. 4 shows additional components that may be included in headpiece module 102 and additional components that may be included in or connected to sound processor module 104. It will be recognized that the additional components shown in FIG. 4 are merely illustrative of the many different components that may be included in or otherwise connected to headpiece module 102 and/or sound processor module 104 as may serve a particular implementation.

As shown in FIG. 4, headpiece module 102 may additionally include a battery 402, a microphone 404, and communication circuitry 406. Each of these components may be communicatively coupled to primary sound processor 108 in any suitable manner.

Battery 402 may include any suitable type of battery and may be configured to provide power to one or more components within headpiece module 102. Battery 402 may additionally or alternatively be configured to provide power to auditory prosthesis 106. For example, power derived from battery 402 may be transmitted to auditory prosthesis by way of communication link 116. Battery 402 may additionally or alternatively be configured to provide power to one or more components included in sound processor module 104. For example, operating power derived from battery 402 may be transmitted to secondary sound processor 110 by way of communication link 118 while sound processor module 104 is communicatively coupled to headpiece module 102. In this manner, sound processor module 104 may not need to include its own separate battery.

Microphone 404 may be configured to receive (e.g., detect) one or more audio signals presented to a patient for processing by primary sound processor 108. Microphone 404 may be at least partially disposed within headpiece module 102, as shown in FIG. 4. Alternatively, microphone 404 may be separate from headpiece module 102 and communicatively coupled to one or more components within headpiece module 102 as may serve a particular implementation.

Communication circuitry 406 may include any suitable combination of components (e.g., one or more coils, transceivers, etc.) configured to facilitate transmission of data in between headpiece module 102 and auditory prosthesis 106 and/or in between headpiece module 102 and sound processor module 104. For example, communication circuitry 406 may be configured to transmit stimulation parameters generated by primary sound processor 108 to auditory prosthesis 106. Additionally or alternatively, communication circuitry 406 may be configured to receive data from secondary sound processor 110 for processing by primary sound processor 108.

As also shown in FIG. 4, sound processor module 104 may additionally include one or more user input mechanisms 408 and one or more interface components 410. Sound processor module 104 may additionally be configured to be selectively and communicatively coupled to an external device 412 and one or more microphones 414 (e.g., microphones 414-1 and 414-2). User input mechanisms 408, interface components 410, external device 412, and microphones 414 may be communicatively coupled to secondary sound processor 110 in any suitable manner as may serve a particular implementation.

User input mechanisms 408 may include one or more mechanisms with which a user (e.g., an auditory prosthesis patient) may interact to provide user input to secondary sound processor 110 and/or primary sound processor 108. For example, user input mechanisms 408 may include a program selection mechanism (e.g., a program selection switch) configured to allow a user to manually direct primary sound processor 108 to switch from operating in accordance with a particular sound processing program to operating in accordance with a different sound processing program. User input mechanisms 408 may additionally or alternatively include a volume control mechanism (e.g., a volume control knob configured to allow a user to adjust one or more volume levels, a sensitivity control mechanism (e.g., a sensitivity control knob) configured to allow a user to adjust one or more sensitivity levels, and/or any other type of user input mechanism as may serve a particular implementation.

Interface components 410 may include any suitable combination of components configured to interface with one or more external devices (i.e., facilitate communication by secondary sound processor 110 and/or primary sound processor 108 with the one or more external devices). For example, interface components 410 may include in or more input ports, communication components, etc. configured to facilitate communicative coupling of sound processor module 104 to the one or more external devices.

To illustrate, interface components 410 may interface with external device 412. External device 412 may include an auxiliary audio input device, a fitting device, a clinician's programming interface device, a hearing instrument body area network ("HiBAN") device, an audio gateway device (e.g., iCOM), a remote control device (e.g., myPilot), or another sound processor (e.g., another sound processor used in a bilateral auditory prosthesis system).

As an example, external device 412 may include an auxiliary audio input device, such as an audio player. To experience audio presented by the auxiliary audio input device, a user may couple sound processor module 104 to headpiece module 102 and then couple the auxiliary audio input device to sound processor module 104 (or in reverse order). Secondary sound processor 110 may then receive audio signals from the auxiliary audio input device by way of interface components 410 and transmit data representative of the received audio signals to primary sound processor 108. In some examples, secondary sound processor 110 may apply one or more pre-processing functions to the audio signals before they are transmitted to primary sound processor 108.

As another example, external device 412 may include a fitting device that may be used by an audiologist or the like to fit primary sound processor 108 to a patient. To this end, sound processor module 104 may be coupled to headpiece module 102. Fitting data may then be relayed from the fitting device to primary sound processor 108 by secondary sound processor 110.

As shown in FIG. 4, multiple microphones 414 may be communicatively coupled to sound processor module 104. Microphones 414 may be placed at any suitable location (e.g., within the opening of the ear). Multiple microphones 414 may facilitate performance of one or more beam forming functions by secondary sound processor 110, which may increase the overall performance of auditory prosthesis system 100. It will be recognized that any number of microphones 414 may be communicatively coupled to sound processor module 104.

Figure 5:
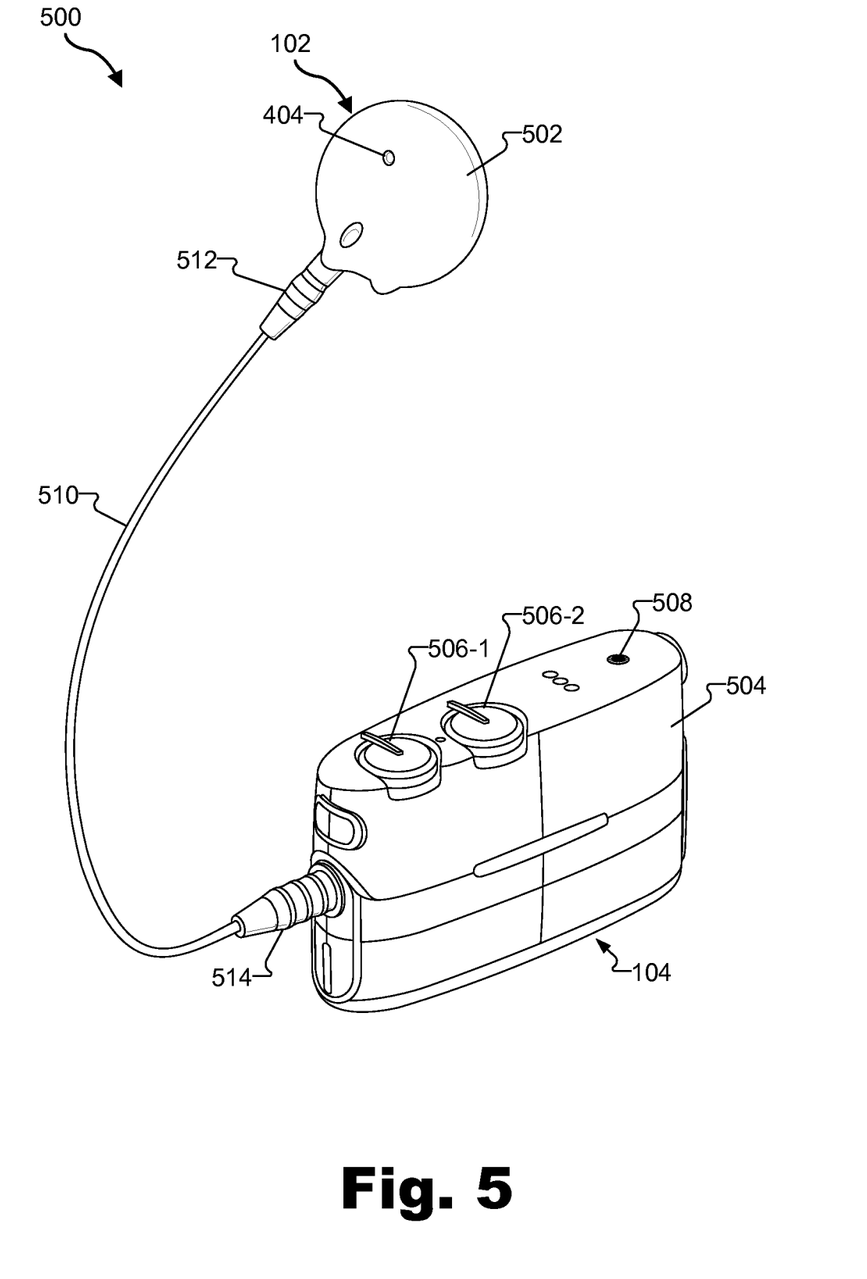

FIG. 5 illustrates an exemplary physical implementation 500 of auditory prosthesis system 100. As shown, headpiece module 102 includes a housing 502 within which various components, including primary sound processor 108, may be disposed. FIG. 5 shows that microphone 404 may be integrated into a surface of housing 502.

As shown, sound processor module 104 includes a device configured to be worn or carried by the patient off the ear. Alternatively, as described above, sound processor 104 may include a behind-the-ear device. As shown, sound processor module 104 includes a housing 504 within which various components, including secondary sound processor 110, may be disposed. User input mechanisms 506-1 and 506-2 (e.g., volume and sensitivity control knobs) and an interface port 508 (e.g., an auxiliary audio input port) may be integrated into a surface of housing 504.

FIG. 5 also shows that sound processor module 104 may be selectively coupled to headpiece module 102. For example, as shown in FIG. 5, sound processor module 104 may be coupled to headpiece module 102 by way of cable 510. To this end, sound processor module 104 and headpiece module 102 may each include a connector port (not shown) configured to connect to corresponding connectors 512 and 514 of cable 510. When a user desires to disconnect sound processor module 104 from headpiece module 102, he or she may remove connector 514 of cable 510 from the connector port of sound processor module 104 and/or connector 512 of cable 510 from the connector port of headpiece module 102. It will be recognized that sound processor module 104 may additionally or alternatively be configured to wirelessly connect to headpiece module 102.

Figure 6:
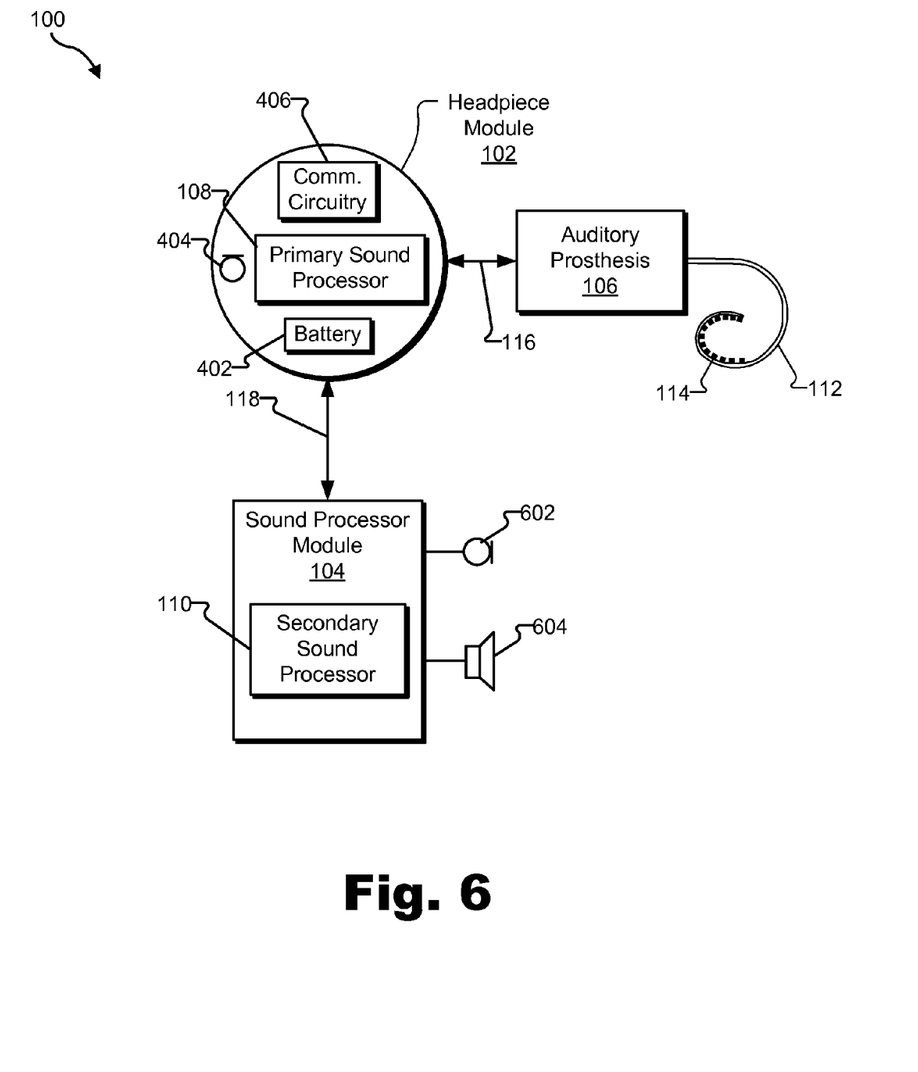

FIG. 6 illustrates another exemplary implementation 600 of auditory prosthesis system 100 wherein sound processor module 104 is configured to provide electro-acoustic stimulation functionality to a user of headpiece module 102. As used herein, "electro-acoustic stimulation" refers to the use of a hearing aid and an auditory prosthesis (e.g., a cochlear implant) together in the same ear. The hearing aid acoustically amplifies the low frequencies while the auditory prosthesis electrically stimulates the high frequencies. The auditory nerve combines the acoustic and electric stimuli to one auditory signal.

To this end, a microphone 602 and a loudspeaker 604 may be communicatively coupled to sound processor module 104. Microphone 602 may be similar in function to microphones 414. Loudspeaker 604 (also referred to as a receiver) may be configured to apply acoustic stimulation to the user. For example, at the direction of secondary sound processor 110, loudspeaker 604 may present an amplified version of audio content included in a low frequency band to the user.

To illustrate, secondary sound processor 110 may detect audio content (e.g., one or more audio signals) presented to the user by way of microphone 602. Secondary sound processor 110 may then determine whether the detected audio content is included in a "high" frequency band (e.g., a frequency band substantially equal to 1 kHz-8 kHz) or in a "low" frequency band (e.g., a frequency band substantially equal to 100 Hz-1 kHz). It will be recognized that the particular frequencies associated with the high and low frequency bands may vary as may serve a particular implementation.

If the audio content is included in the high frequency band, secondary sound processor 110 may transmit data representative of the audio content to primary sound processor 108 or otherwise instruct primary sound processor 108 to direct auditory prosthesis 106 to apply electrical representative of the audio content to the user. Alternatively, if the audio content is included in the low frequency band, secondary sound processor 110 may direct loudspeaker 604 to apply acoustic stimulation representative of the audio content to the patient.

It will be recognized that the electro-acoustic stimulation functionality of sound processor module 104 described in FIG. 6 may be combined with the functionality of sound processor module 104 described in FIG. 4. Sound processor module 104 may provide additional or alternative functionality as may serve a particular implementation.

Figure 7:
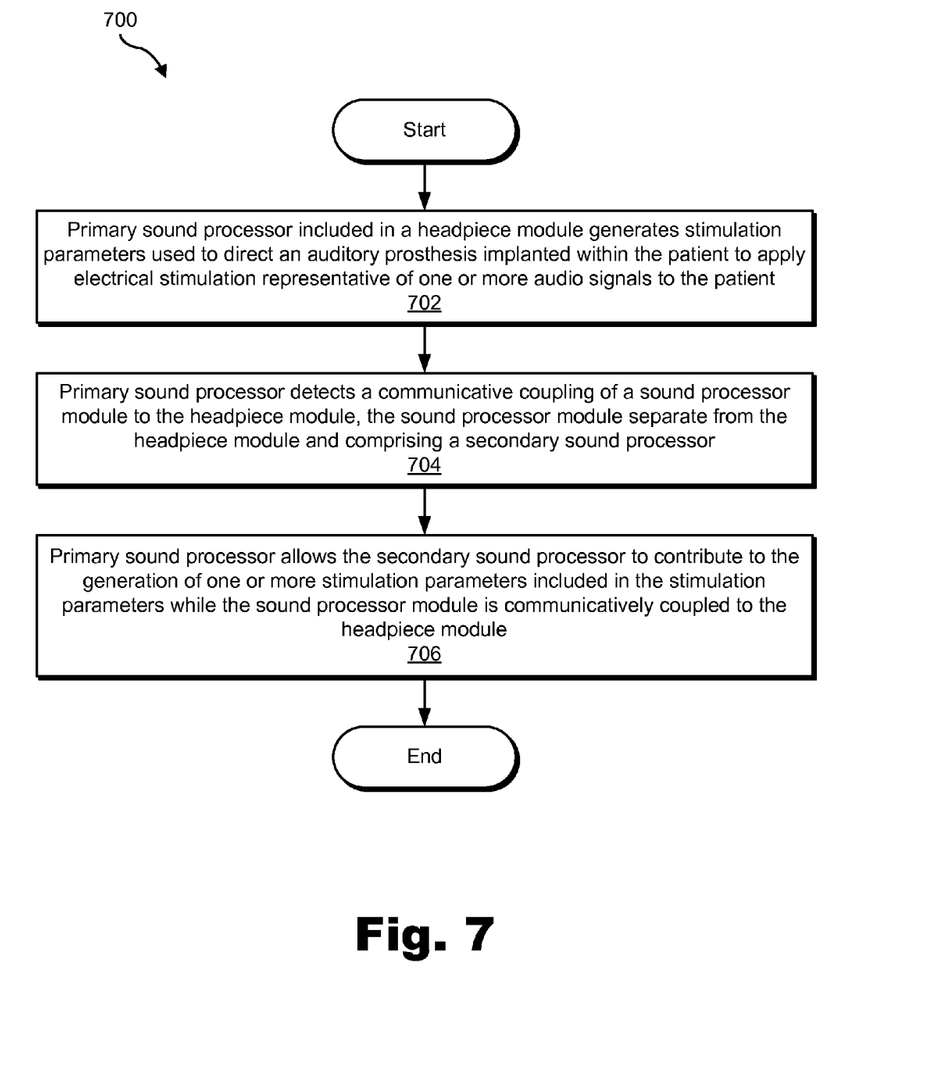
FIG. 7 illustrates an exemplary method according to principles described herein.

FIG. 7 illustrates an exemplary method 700 in accordance with the systems described herein. While FIG. 7 illustrates exemplary steps according to one embodiment, other embodiments may omit, add to, reorder, and/or modify any of the steps shown in FIG. 7. One or more of the steps shown in FIG. 7 may be performed by any component or combination of components of primary sound processor 108.

In step 702, a primary sound processor included in a headpiece module generates stimulation parameters used to direct an auditory prosthesis implanted within the patient to apply electrical stimulation representative of one or more audio signals to the patient. Step 702 may be performed in any of the ways described herein.

In step 704, the primary sound processor detects a communicative coupling of a sound processor module to the headpiece module. The sound processor module is separate from the headpiece module and comprises a secondary sound processor. Step 704 may be performed in any of the ways described herein.

In step 706, the primary sound processor allows the secondary sound processor to contribute to the generation of one or more stimulation parameters included in the stimulation parameters while the sound processor module is communicatively coupled to the headpiece module. Step 706 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    an off-the-ear headpiece module configured to be affixed to a head of a patient and comprising
        a primary sound processor that generates stimulation parameters used to direct an auditory prosthesis implanted within the patient to apply electrical stimulation representative of one or more audio signals to the patient; and
        a battery that provides operating power to the primary sound processor; and
    a sound processor module separate from the headpiece module and that does not include a separate battery and that is configured to be selectively and communicatively coupled to the headpiece module, the sound processor module comprising a secondary sound processor that contributes to the generation of one or more stimulation parameters included in the stimulation parameters while the sound processor module is communicatively coupled to the headpiece module;
    wherein the primary sound processor
        generates the stimulation parameters independent of the secondary sound processor while the sound processor module is not communicatively coupled to the headpiece module, and
        provides, while the sound processor module is communicatively coupled to the headpiece module, operating power to the secondary sound processor from the battery included in the headpiece module.

2. The system of claim 1, wherein the primary sound processor generates one or more of the stimulation parameters independent of the secondary sound processor while the sound processor module is communicatively coupled to the headpiece module.

3. The system of claim 1, wherein the sound processor module comprises one or more user input mechanisms, and wherein the secondary sound processor contributes to the generation of the one or more stimulation parameters by
    detecting interaction by a user with the one or more user input mechanisms; and
    adjusting the one or more stimulation parameters in response to the interaction by the user with the one or more user input mechanisms.

4. The system of claim 3, wherein the one or more user input mechanisms comprise at least one of a program selection mechanism, a volume control mechanism, and a sensitivity control mechanism.

5. The system of claim 1, wherein the one or more stimulation parameters are associated with an audio signal included in the one or more audio signals, and wherein the secondary sound processor contributes to the generation of the one or more stimulation parameters by:
    detecting the audio signal;
    applying one or more pre-processing functions to the audio signal; and
    transmitting data representative of the pre-processed audio signal to the primary sound processor.

6. The system of claim 5, wherein the sound processor module is communicatively coupled to one or more microphones, and wherein the secondary sound processor detects the audio signal using the one or more microphones.

7. The system of claim 6, wherein the one or more pre-processing functions comprises a beam forming function associated with the detection of the audio signals using the one or more microphones.

8. The system of claim 1, wherein the sound processor module further comprises one or more interface components that facilitate communication by the secondary sound processor with one or more auxiliary audio input devices, and wherein the secondary sound processor contributes to the generation of the one or more stimulation parameters by:
    receiving, by way of the one or more interface components, an audio signal included in the one or more audio signals from one of the one or more auxiliary audio input devices; and
    transmitting data representative of the received audio signal to the primary sound processor.

9. The system of claim 8, wherein the primary sound processor generates one or more stimulation parameters associated with the received audio signal in accordance with the transmitted data.

10. The system of claim 8, wherein the one or more auxiliary audio input devices comprise at least one of an FM transmitter, a Bluetooth device, and an audio player.

11. The system of claim 1, wherein the sound processor module further comprises one or more interface components that facilitate communication by the secondary sound processor with at least one of a hearing instrument body area network device, an audio gateway device, a remote control device, and another third sound processor.

12. The system of claim 1, wherein:
    the sound processor module further comprises one or more interface components that facilitate communication by the secondary sound processor with a fitting device; and
    the secondary sound processor relays fitting data received from the fitting device to the primary sound processor.

13. The system of claim 1, wherein
the sound processor module is communicatively coupled to a loudspeaker; and
the secondary sound processor directs the loudspeaker to apply acoustic stimulation representative of at least one of the one or more audio signals to the patient.

14. The system of claim 1, wherein the headpiece module further comprises communication circuitry that transmits the stimulation parameters to the auditory prosthesis.

15. The system of claim 1, wherein the sound processor module is configured to be selectively and communicatively coupled to the headpiece module by way of at least one of a wired communication link and a wireless communication link.

16. The system of claim 1, wherein the sound processor module comprises at least one of a behind-the-ear sound processor module and an off-the-ear sound processor module.

17. An off-the ear headpiece module configured to be affixed to a head of a patient and comprising:
- a primary sound processor that generates stimulation parameters used to direct an auditory prosthesis implanted within the patient to apply electrical stimulation representative of one or more audio signals to the patient;
- communication circuitry communicatively coupled to the primary sound processor and that transmits the stimulation parameters to the auditory prosthesis; and
- a battery that provides operating power to the primary sound processor
wherein the primary sound processor
- detects a communicative coupling of a sound processor module to the headpiece module, wherein the sound processor module does not include a separate battery, is separate from the headpiece module, and comprises a secondary sound processor,
- allows the secondary sound processor to contribute to the generation of one or more stimulation parameters included in the stimulation parameters while the sound processor module is communicatively coupled to the headpiece module,
- detects that the sound processor module is not communicatively coupled to the headpiece module,
- generates the stimulation parameters independent of the secondary sound processor while the sound processor module is not communicatively coupled to the headpiece module, and
- provides, while the sound processor module is communicatively coupled to the headpiece module, operating power to the secondary sound processor from the battery included in the headpiece module.

18. A method comprising:
generating, by a primary sound processor included in an off-the-ear headpiece module configured to be affixed to a head of a patient, stimulation parameters used to direct an auditory prosthesis implanted within the patient to apply electrical stimulation representative of one or more audio signals to the patient, the headpiece module including a battery that provides operating power to the primary sound processor;

allowing, by the primary sound processor, a secondary sound processor included in a sound processor module separate from the headpiece module and that does not have a separate battery, to contribute to the generation of one or more stimulation parameters included in the stimulation parameters while the sound processor module is communicatively coupled to the headpiece module;

generating, by the primary sound processor, the stimulation parameters independent of the secondary sound processor while the sound processor module is not communicatively coupled to the headpiece module; and providing, by the primary sound processor while the sound processor module is communicatively coupled to the headpiece module, operating power to the secondary sound processor from the battery included in the headpiece module.

* * * * *